United States Patent

Büyüktimkin et al.

Patent Number: 6,083,996
Date of Patent: Jul. 4, 2000

[54] TOPICAL COMPOSITIONS FOR NSAI DRUG DELIVERY

[75] Inventors: Servet Büyüktimkin; Nadir Büyüktimkin, both of Lawrence, Kans.; James Yeager, Deerfield, Ill.

[73] Assignee: NexMed Holdings, Inc., Robbinsville, N.J.

[21] Appl. No.: 08/965,001

[22] Filed: Nov. 5, 1997

[51] Int. Cl.[7] .............................. A61K 9/10; A61K 47/14; A61K 47/10

[52] U.S. Cl. ....................... 514/772.6; 514/781; 514/782; 514/785

[58] Field of Search .......................... 424/449; 514/772.6

[56] References Cited

U.S. PATENT DOCUMENTS

| | | | |
|---|---|---|---|
| 4,393,076 | 7/1983 | Noda et al. | 424/317 |
| 4,771,004 | 9/1988 | Higuchi | 436/5 |
| 4,923,898 | 5/1990 | Sunshine et al. | 514/557 |
| 4,980,378 | 12/1990 | Wong et al. | 514/785 |
| 5,082,866 | 1/1992 | Wong et al. | 514/785 |
| 5,093,133 | 3/1992 | Wisniewski et al. | 424/484 |
| 5,210,009 | 5/1993 | Mody et al. | 514/557 |
| 5,527,832 | 6/1996 | Chi et al. | 514/772.4 |
| 5,534,260 | 7/1996 | Petersen et al. | 424/448 |
| 5,654,337 | 8/1997 | Roentsch et al. | 514/570 |

OTHER PUBLICATIONS

Article, "Alkyl N,N–Disubstituted–Amino Acetates", Büyüktimkin, N., et al., pp. 91–102, appearing in "Percutaneous Penetration Enhancers," 1995 by CRC Press, Inc.

*Primary Examiner*—Peter F. Kulkosky
*Attorney, Agent, or Firm*—Olson & Hierl, Ltd.

[57] ABSTRACT

An aqueous pharmaceutical composition of a semi-solid consistency is provided for topical application of non-steroidal anti-inflammatory (NSAI) drugs. The composition comprises one or more NSAI drugs, a non-basic polymeric skin penetration enhancer and a lipophilic solvent. The polymeric skin penetration enhancer is present in an amount sufficient to enhance skin penetration of the NSAI drug. The lipophilic solvent is a mixture of an aliphatic $C_2$ to $C_8$ alcohol and an aliphatic $C_8$ to $C_{30}$ ester.

18 Claims, 10 Drawing Sheets

TOPICAL COMPOSITIONS FOR NSAI DRUG DELIVERY

TECHNICAL FIELD OF THE INVENTION

This invention relates to aqueous pharmaceutical compositions for transdermal administration of non-steroidal anti-inflammatory drugs to a patient.

BACKGROUND OF THE INVENTION

Non-steroidal anti-inflammatory (hereafter NSAI) drugs have been used extensively in recent years for treatment of chronic rheumatic or arthritic conditions and for management of pain. The compounds are believed to bring relief by inhibiting biosynthesis of prostaglandins at affected joints or in other tissue areas. Salicylic acid, or aspirin, and ibuprofen are well-known examples of NSAI drugs.

Patients taking NSAI drugs orally face an increased risk for peptic ulcers and gastrointestinal blood loss resulting in anemia. Such adverse reactions especially plague patients taking NSAI drugs over prolonged periods. One solution to the gastrointestinal complications problem is to deliver the NSAI drug transdermally via a topical preparation rather than orally. Transdermal drug delivery provides other benefits as well, these include less frequent dosing, better controlled drug release, and a greater ability to target delivery to specific tissue sites.

Working alone most drugs, NSAI drugs included, do not sufficiently permeate the skin to provide drug concentration levels comparable to those obtained from oral delivery. To overcome this problem, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not affect available dosage forms (e.g. cream or gel), or the odor of the topical composition.

A wide variety of compounds have been evaluated as to their effectiveness in enhancing the rate of penetration of drugs through the skin. See, for example, *Percutaneous Penetration Enhancers*, Maibach, H. I. and Smith, H. E. (eds.), CRC Press, Inc., Boca Raton, Fla. (1995), which surveys the use and the testing of various skin penetration enhancers.

Efforts at providing effective transdermal delivery of NSAI drugs are reflected in various NSAI creams and gels having such penetration enhancers. For example, U.S. Pat. No. 5,210,099 to Mody et al. discloses an oil-in-water emulsion cream having crystalline form ibuprofen suspended in the oil phase with a variety of penetration enhancers. U.S. Pat. No. 5,093,133 to Wisniewski et al. is directed to the S-enantiomer (optical isomer) of ibuprofen in a hydroalcoholic gel, where the alcohol component is said to enhance drug absorption. U.S. Pat. No. 4,393,076 to Noda et al. is directed to a neutralized ketoprofen gel containing a glycol-lower alcohol mixture.

These and other conventional compositions suffer from one or more serious drawbacks as follows: complicated and expensive preparation steps or ingredients, wasteful drug overloading requirements, and insufficient drug penetration.

Thus, there continues to be a need for improved, cost-effective compositions for transdermal drug delivery of NSAI drugs.

SUMMARY OF THE INVENTION

An aqueous pharmaceutical composition of a semi-solid consistency suitable for topical application comprises a non-steroidal anti-inflammatory (NSAI) drug, a non-basic polymeric skin penetration enhancer and a lipophilic solvent. The polymeric skin penetration enhancer is present in the composition in an amount sufficient to enhance skin penetration of the NSAI drug. Preferred are either a water-dispersible non-basic (acidic or neutral) polymer or a polysaccharide, or a mixture thereof. The lipophilic solvent is a mixture of an aliphatic $C_2$ to $C_8$ alcohol and an aliphatic $C_8$ to $C_{30}$ ester.

The composition may also include a thickening agent, an emulsifying agent and/or a buffer system capable of providing a buffered pH value for the composition in the range of about 3 to physiological.

In a preferred composition, the NSAI drug is an ibufenac group drug and the polymeric skin penetration enhancer is a galactomannan gum.

DETAILED DESCRIPTION OF THE INVENTION

Figure 1:
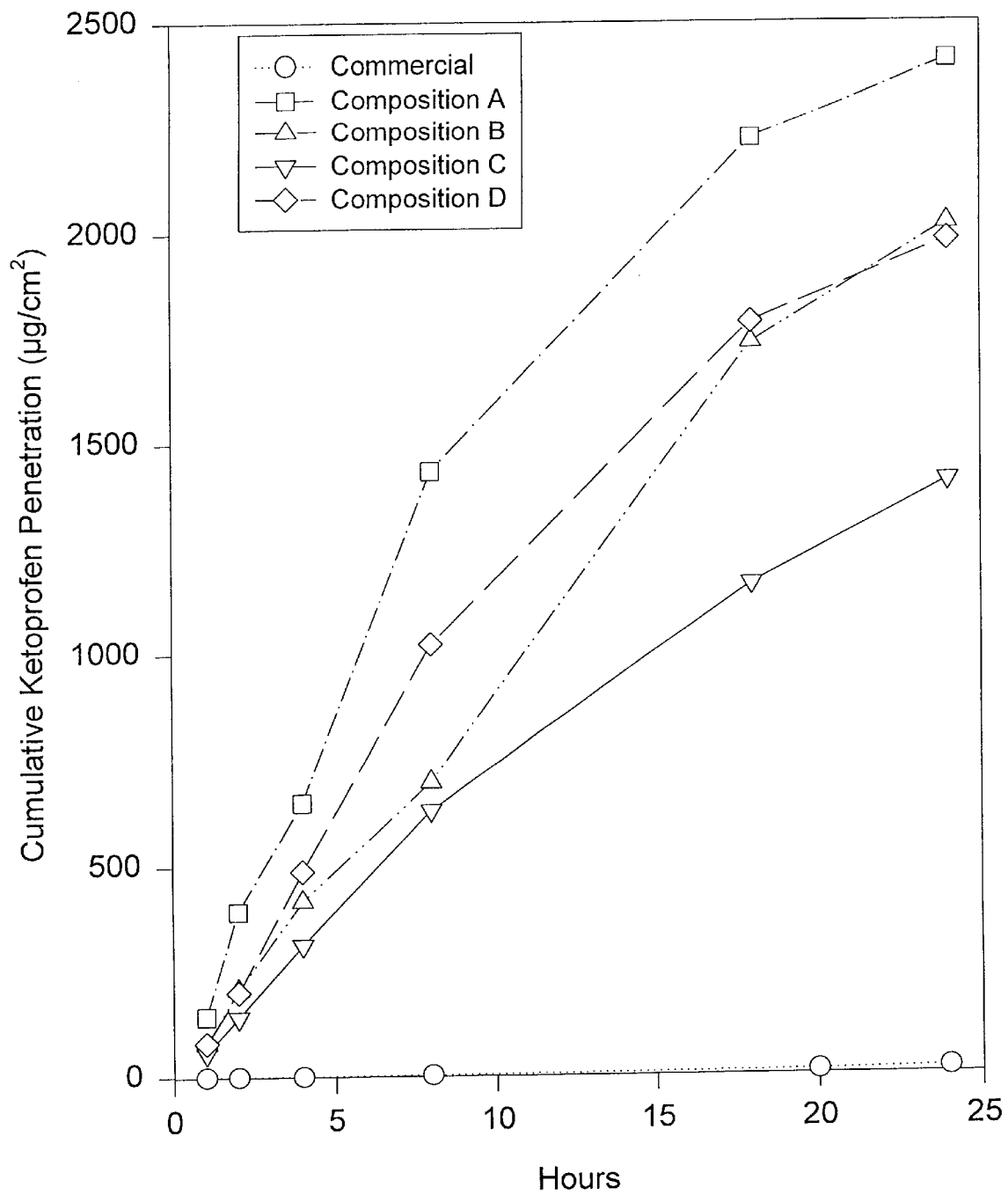
FIG. 1 is a graph of the cumulative drug penetration through shed snake skin of a commercial ketoprofen composition and four ketoprofen compositions (A through D) prepared according to the present invention.

The pharmaceutical composition of the present invention comprises a NSAI drug, a non-basic (i.e. acid or neutral)

polymeric skin penetration enhancer, and a co-acting lipophilic solvent. As prepared, this composition forms a semisolid suitable for topical application. Acid buffer systems and stabilizers may be added as necessary. In use as a topical agent, the composition of the present invention exhibits relatively high NSAI drug penetration and bioavailability without requiring a wasteful overloading drug concentration. The composition further exhibits reduced skin irritation, sensitivity and damage.

The invented composition includes one or more NSAI drugs. Although most are organic acids, the NSAI group embraces a wide range of chemical structures. One common approach divides the NSAI drugs as follows:

(1) salicylic acid derivatives, which includes aspirin;
(2) propionic acids, which includes ibuprofen, ketoprofen, oxaprozin, pirprofen, indobufen, tiaprofenic acid;
(3) para-aminophenol derivatives, which includes acetaminophen;
(4) indole and indene acetic acids, which includes indomethacin, sulindac, etodolac, carprofen;
(5) heteroaryl acetic acids, which includes diclofenac, tolmetin, ketorolac;
(6) anthranilic acids (or fenamates), which includes mefenanamic acid, etofenamat;
(7) enolic acids, which includes piroxicam, meloxicam, tenoxicam; and
(8) alkanones.

The above groups are described in Chapter 27 of *Goodman and Gilman's The Pharmacological Basis of Therapeutics*, 9th Ed., McGraw-Hill Inc., New York, N.Y. (1995). The *Cutting's Handbook of Pharmacology* characterizes the ibufenac group, a grouping of NSAI drugs based on structural relationship to ibufenac:

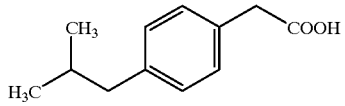

[*Cutting's Handbook of Pharmacology*, 7th Ed., Whitehouse Station, Appleton-Century-Crotts, Conn. (1984), pp. 615–617.] The ibufenac group includes, inter alia, both the salicylic acid derivatives and propionic acids group. Ibufenac group drugs are preferred for this invention. Examples of suitable ibufenac group drugs include cliprofen, fenoprofen, flurbiprofen, ibuprofen, ketoprofen, fenbufen, alcofenac, amfenac sodium, fenclofenac, naproxen, naproxol, and diflunisal. Among ibufenac group drugs, ketoprofen is most preferred.

Specific compounds falling within the foregoing classes of NSAI drugs are well known to those skilled in the art and reference may be had to various literature references for their chemical structures, pharmacological activities, side effects, and normal oral dosage ranges. See for example, *Physician's Desk Reference*, 51st Ed. (1997), *The Merck Index*, 12th Ed., Merck & Co., N.J. (1996), and *Martindale The Extra Pharmacopoeia*, 28th Ed., London, The Pharmaceutical Press (1982).

Structural formulas for representative ibufenac group drugs are set forth below:

ibufenac:

ibuprofen:

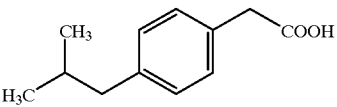

alcofenac:

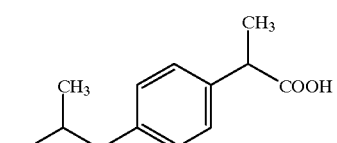

ketoprofen:

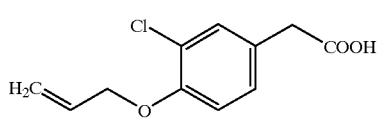

flurbiprofen:

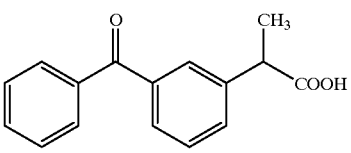

fenoprofen:

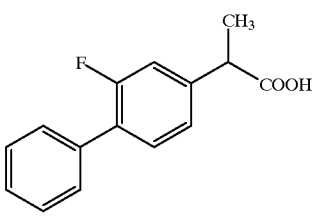

naproxen:

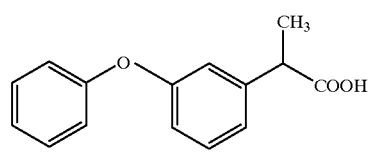

fenbufen:

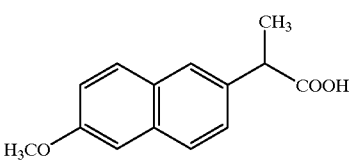

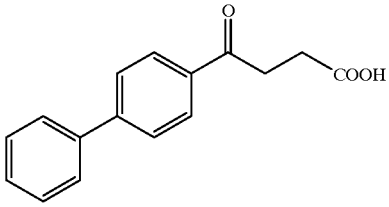

Compounds referenced herein are intended to encompass pharmaceutically acceptable derivatives of the compound, including acceptable salts such as sodium salts.

Preferred among the enolic acids group is piroxicam:

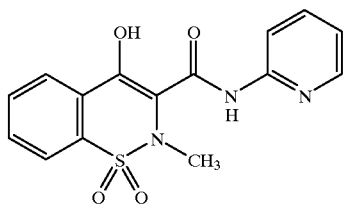

The quantity of NSAI drug in the pharmaceutical compositions of the present invention varies according to the desired dose, the solubility of. the NSAI drug, and the dosage form (e.g., suppository or topical gel). The composition preferably contains between about 0.1 percent to about 10 percent NSAI drug by weight and most preferably from 0.5 percent to 10 percent based on the total weight of the composition.

An important component of the invention is the polymeric skin penetration enhancer. As used herein, the term skin penetration enhancer means a substance that promotes drug diffusion through the skin. The polymeric skin penetration enhancer is non-basic, i.e. acid or neutral, and present in an amount sufficient to enhance the penetration of the selected NSAI drug or drug combination. The specific amount varies according to the type of enhancer, the type of NSAI drug, and the desired release rate.

The polymeric skin penetration enhancer preferably is a water-dispersible acid polymer or a polysaccharide gum, or a mixture of both. An illustrative water-soluble acid polymer is a polyacrylic acid polymer. One type of polyacrylic acid polymer formulation suitable for use in practicing this invention is known generically as "carbomer." Carbomer is polyacrylic acid polymers lightly cross-linked with polyalkenyl polyether. It is commercially available from the B. F. Goodrich Company (Akron, Ohio) under the designation "CARBOPOL™." A particularly preferred variety of carbomer is that designated as "CARBOPOL 940P."

Other polyacrylic acid polymers suitable for use in practicing this invention are those commercially available under the designations "Pemulen™" (B. F. Goodrich Company) and "POLYCARBOPHIL™" (A. H. Robbins, Richmond, Va.). The Pemulen™ polymers are copolymers of $C_{10}$ to $C_{30}$ alkyl acrylates and one or more monomers of acrylic acid, methacrylic acid or one of their simple esters crosslinked with an allyl ether of sucrose or an allyl ether of pentaerythritol. The POLYCARBOPHIL™ enhancer is a polyacrylic acid cross-linked with divinyl glycol.

Where polyacrylic acid polymers serve as the penetration enhancer, they represent about 0.5 weight percent to about 5 weight percent of the pharmaceutical compositions of the present invention, and preferably about 2 weight percent to about 3 weight percent, based on the total weight of the composition. The polyacrylic acid polymers preferably are maintained at an acidic or neutral pH.

Polysaccharide gums also may serve as penetration enhancers in the composition of the present invention. Suitable representative gums are those in the xanthan gum category and the galactomannan gum category. Gums, and galactomannan gums in particular, are well-known materials. See for instance, *Industrial Gums: Polysaccharides & Their Derivatives*, Whistler R. L., BeMiller J. N. (eds.), 3rd Ed. Academic Press (1992) and Davidson, R. L., *Handbook of Water-Soluble Gums & Resins*, McGraw-Hill, Inc., N.Y. (1980).

A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→4). Single membered α-D-mannopyranosyl units, linked (1→6) with the main chain, are present as side branches. Galactomannan gums include guar gum, which is the pulverized endosperm of the seed of either of two leguminous plants (*cyamposis tetragonalobus* and *psoraloids*) and locust bean gum, which is found in the endosperm of the seeds of the carob tree (*ceratonia siliqua*). Carob gum is also a galactomannan.

Other suitable representative gums include agar gum, alginate, carrageenan gum, ghatti gum, karaya gum, kadaya gum, rhamsan gum, xanthan gum and derivatives of galactomannan polymers.

Xanthan gum is a high-molecular-weight natural carbohydrate produced in culture fermentation by the microorganism *Xanthomonas campestris*. Xanthan gum contains three different monosaccharides: mannose, glucose, and glucuronic acid (as a mixed potassium, sodium, and calcium salt). Each repeating block of the polymer chain has five sugar units (two glucose, two mannose, one glucuronic acid). The polymer's main chain is made up of β-D-glucose units linked through the 1- and 4-positions; thus, the chemical structure of the main chain is identical to that of cellulose.

Also a polysaccharide, alginates are salts of alginic acid. Alginic acid comprises D-mannuronic acid and L-gluronic acid residues and has three kinds of polymer segments: one consisting of D-mannuronic acid units, a second of L-gluronic acid units, and the third of alternating D-mannuronic acid and L-gluronic acid residues. Conventionally known as propylene glycol alginate, the propylene glycol ester of alginic acid is the preferred form alginate for the present invention.

The composition of the present invention may also contain a mixture of various gums (or their derivatives), or mixture of gums and acidic polymers.

Where polysaccharide gums serve as the penetration enhancers, they represent about 1 weight percent to about 5 weight percent, based on the total weight of the composition. Illustrative compositions are given in the examples, below.

Other suitable polymeric skin penetration enhancers are cellulose derivatives, such as ethyl cellulose, methyl cellulose, hydroxypropyl cellulose.

Additionally, known transdermal penetration enhancers can also be added, if desired. Illustrative are dimethyl sulfoxide (DMSO) and dimethyl acetamide (DMA), 2-pyrrolidone, N,N-diethyl-m-toluamide (DEET), 1-dodecylazacycloheptane-2-one (Azone®, a registered trademark of Nelson Research), N,N-dimethylformamide, N-methyl-2-pyrrolidone, calcium thioglycolate and other enhancers such as dioxolanes, cyclic ketones, and their derivatives and so on. Also illustrative are a group of biodegradable absorption enhancers which are alkyl N,N-2-(disubstituted amino) alkanoates as reported in U.S. Pat. No. 4,980,378 and U.S. Pat. No. 5,082,866, both to Wong et al. Preferred supplemental enhancers are alkyl 2-(N,N-disubstituted amino)-alkanoates, (N,N-disubstituted amino)-alkanol alkanoates, and a mixture of these.

Another important component of the present invention is a lipophilic solvent. The term lipophilic solvent as used herein refers to an agent that is lipophilic as well as hydrophilic and an NSAI drug solvent. The lipophilic solvent is a mixture of one or more aliphatic $C_1$ to $C_8$ alcohols with one or more aliphatic $C_8$ to $C_{30}$ esters. Illustrative suitable alcohols are ethanol, n-propanol, isopropanol, glycerol, and propylene glycol while suitable esters are ethyl acetate, butyl acetate, ethyl laurate, methyl propionate, isopropyl myristate and isopropyl palmitate. Preferred are mixtures of ethanol, isopropanol or propylene glycol with isopropyl myristate.

The concentration of lipophilic solvent required necessarily varies according to other factors such as the solubility of the NSAI drug, the desired semi-solid consistency, and desired skin penetration promoting effects. A preferred pharmaceutical composition embodying the present invention contains lipophilic solvent in the range of about 10 percent to about 40 percent by weight based on the total weight of the composition. Where a mixture of aliphatic alcohol and aliphatic ester are employed, the preferred amount of alcohol is in the range of about 10 percent to about 35 percent, while that of aliphatic ester is in the range from about 5 percent to about 10 percent.

An optional but preferred component of the present invention is an acid buffer system. Acid buffer systems serve to maintain or buffer the pH of compositions within a desired range.

The final pH value of the pharmaceutical composition of the present invention may vary within the physiologically tolerable range. Necessarily, the final pH value is not irritating to human skin. Without violating this constraint, the pH may be selected to improve NSAI drug solubility, optimize skin penetration rate or adjust consistency when required. Any suitable method of adjusting the pH value of the aqueous solutions may be used, for example, by a buffer system, or an organic base such as triethanol amine, isopropylamine, or the like, or an inorganic base such as sodium hydroxide (NaOH). With these factors accounted for, the preferred pH value is about 3 to physiological. Where ketoprofen is the NSAI drug, the preferred pH range is from about 4.5 to about 5.5.

The term "buffer system" or "buffer" as used herein has reference to a solute agent or agents which, when in a water solution, stabilize such solution against a major change in pH (or hydrogen ion concentration or activity) when acids or bases are added thereto. Solute agent or agents which are thus responsible for a resistance to change in pH from a starting buffered pH value in the range indicated above are well known.

The remaining component of the composition is water. The composition contains water in the range of about 60 to about 90 percent, based on the total weight of the composition. The specific amount of water present is not critical, however, being adjustable to obtain the desired consistency and/or concentration of the other components.

Contemplated dosage forms of the semi-solid pharmaceutical composition of the present invention are creams, gels, and the like, also including but not limited to compositions suitable for use with transdermal patches and like devices.

The ingredients listed above may be combined in any order and manner that produces a composition comprising an NSAI drug dissolved in, and evenly dispersed, throughout a one-phase aqueous semi-solid. One available approach to preparing such compositions involves preparation of an aqueous solution of the polymeric skin penetration enhancer, which will be called "Part A." Advantageously, this solution comprises the polymer in distilled water. To form Part A, the desired amount of skin penetration enhancer is weighed and dispersed in water or a suitably buffered aqueous system. For part B, the desired amount of NSAI drug is weighed and dissolved with the desired amount of the lipophilic solvent. Heat and rigorous agitation may be used to effect complete dissolution of the NSAI drug. Mixing of Parts A and B is followed optionally by neutralization and pH, which results in gelling of the composition. The optional buffer system is a phosphate buffer.

The resulting homogeneous gels, when compared to heretofore available NSAI topical composition, exhibit the advantageous properties described above, including improved NSAI drug permeation and bioavailability without drug overloading, reduced skin damage and related inflammation, and increased flexibility in design of dosage forms. These compositions can be used for prolonged treatment of arthritis and other disorders treated by NSAI drugs, while avoiding the gastrointestinal complications associated with oral dose delivery. Application of NSAI drugs in a topical composition of the present invention to the skin of a patient allows a predetermined amount of the NSAI drug to be administered continuously to the patient and avoids undesirable effects present with a single or multiple administrations of larger dosages. By maintaining a sustained dosage rate, the NSAI drug level in the patient's blood can be better maintained within the optimal therapeutic range.

The practice of the present invention is demonstrated in the following examples. These examples are meant to illustrate the invention rather than to limit its scope. Variations in the treating compositions which do not adversely affect the effectiveness of the NSAI drug will be evident to one skilled in the art, and are within the scope of this invention. For example, additional ingredients such as coloring agents, and the like may be included in the compositions as long as the resulting composition retains desirable properties, as described above. Unless otherwise indicated, each composition is prepared by conventionally admixing the respective indicated components together. Also, unless otherwise indicated, each composition is prepared using a buffer (buffer system) which in use provides a pH value in the range of about 3 to physiological.

EXAMPLE 1

Ketoprofen Composition A

Composition A was prepared as follows. Part A was formed when two parts polymeric skin penetration enhancer (polyacrylic acid polymer, CARBOPOL 940®) were dissolved in 60.5 ml of nanopure water. Part B was prepared by mixing 30 parts of ethanol, 5 parts of isopropyl myristate, and 2.5 parts of ketoprofen. Parts A and B were then thoroughly mixed. TABLE 1, below, contains a list of ingredients.

The resulting composition was evaluated for skin penetration using shed snake skin as a model barrier. Shed snake skin was obtained from the Animal Care Unit of the University of Kansas. With head and tail sections removed, the skin was randomly divided into test sections and then hydrated by soaking.

The samples were then evaluated using Franz-type Diffusion Cells (surface area 1.8 $cm^2$). Specifically, skin pieces were mounted on top of a receptor cell of a vertical diffusion cell assembly in which a small magnetic bar was inserted and filled with an isotonic buffer. A seal was placed on top of the skin section followed by a donor cell. The two cells were then clamped together. Known amounts of the formulations were applied on the bottom of a small capped vial (weight ~5 grams) which fits exactly to the donor cell to ensure uniform distribution. The vials were placed on the skin in the donor cell. To reduce the evaporation of the ingredients, the donor cell and vial were gently taped together with a water-resistant adhesive band. The cells were transferred to a stirred water bath (32° C.). Samples were withdrawn from the cells periodically and analyzed for the concentration of NSAI drug, with changes in concentration indicating the amount penetrating.

For a discussion of the use of shed snake skin in the evaluation of drug penetration, see U.S. Pat. No. 4,771,004 to Higuchi, which is incorporated here by reference to the extent that it is not inconsistent.

The penetration of ketoprofen from Composition A was compared to a commercial topical ketoprofen composition (Profenid, Rhone-Poulenc Rorer). Tests with multiple skin samples yielded data for averaging.

The ketoprofen of Composition A penetrated relatively faster compared to the commercial composition. The results of the penetration study are presented in TABLE 6, below, and in FIG. 1.

EXAMPLE 2

Ketoprofen Composition B

Composition B was prepared using the ingredients listed in TABLE 1, below. The polymeric skin penetration enhancer used was polyacrylic acid polymer (CARBOPOL® 940). The lipophilic solvent used was a mixture of ethanol and ethyl laurate. Ketoprofen skin penetration was measured as described in EXAMPLE 1. The results are presented in TABLE 6, below, and in FIG. 1.

Composition B penetrated relatively faster compared to the commercial composition.

EXAMPLE 3

Ketoprofen Composition C

Composition C was prepared using the ingredients listed in TABLE 1, below. The polymeric skin penetration enhancer used was polyacrylic acid polymer (CARBOPOL® 940). The lipophilic solvent used was a mixture of ethanol, glycerol, and isopropyl myristate. Ketoprofen skin penetration was measured as described in EXAMPLE 1. The results are presented in TABLE 6, below, and in FIG. 1.

Composition C penetrated relatively faster compared to the commercial composition.

EXAMPLE 4

Ketoprofen Composition D

Composition D was prepared using the ingredients listed in TABLE 1, below. The polymeric skin penetration enhancer used was polyacrylic acid polymer (CARBOPOL® 940). The lipophilic solvent used was a mixture of isopropanol and isopropyl myristate. Skin penetration was measured as described in EXAMPLE 1. The results are presented in TABLE 6, below, and in FIG. 1

TABLE 1

| | Ketoprofen Polyacrylic Acid Compositions | | | | |
|---|---|---|---|---|---|
| | Ingredient (wt%) | A | B | C | D |
| Part A: | CARBOPOL 940 ® | 2 | 2 | 2 | 2 |
| | water | 61 | 61 | 61 | 61 |
| Part B: | ketoprofen | 2.5 | 2.5 | 2.5 | 2.5 |
| | ethanol | 30 | 30 | 15 | — |

TABLE 1-continued

| Ketoprofen Polyacrylic Acid Compositions | | | | |
|---|---|---|---|---|
| Ingredient (wt%) | A | B | C | D |
| isopropanol | — | — | — | 30 |
| glycerol | — | — | 15 | — |
| isopropyl myristate | 5 | — | 5 | 5 |
| ethyl laurate | — | 5 | — | — |

EXAMPLE 5

Ketoprofen Composition E

Figure 2:
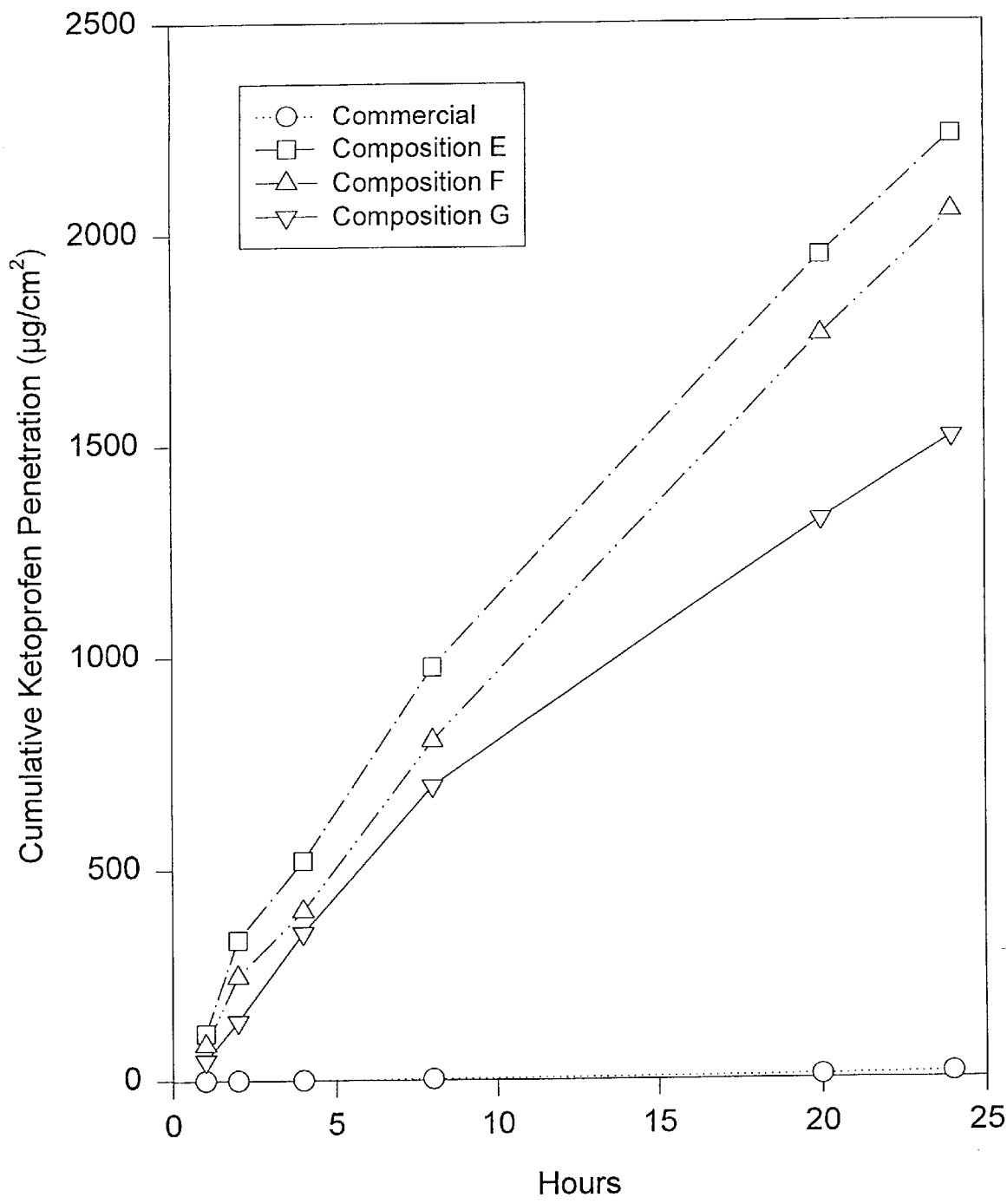
FIG. 2 is a graph of the cumulative drug penetration through shed snake skin of three additional example compositions (E through G) and the same commercial ketoprofen composition.

Composition E was prepared using the ingredients listed in TABLE 2, below. The polymeric skin penetration enhancer used was the galactomannan gum, locust bean gum. The lipophilic solvent used was a mixture of ethanol and isopropyl myristate. Ketoprofen skin penetration was measured as described in EXAMPLE 1. The results are presented in TABLE 6, below, and in FIG. 2.

EXAMPLE 6

Ketoprofen Composition F

Composition F was prepared using the ingredients listed in TABLE 2, below. The polymeric skin penetration enhancer used was the galactomannan gum, locust bean gum. The lipophilic solvent used was a mixture of ethanol and isopropyl myristate. Ketoprofen skin penetration was measured as described in EXAMPLE 1. The results are presented in TABLE 6, below, and in FIG. 2.

EXAMPLE 7

Ketoprofen Composition G

Composition G was prepared using the ingredients listed in TABLE 2, below. The polymeric skin penetration enhancer used was prehydrated locust bean gum. The lipophilic solvent used was a mixture of ethanol and isopropyl myristate. Sucrose stearate was included in Composition G as a preservative. Ketoprofen skin penetration was measured as described in EXAMPLE 1. The results are presented in TABLE 6, below, and in FIG. 2.

TABLE 2

| | Ketoprofen Locust Bean Gum Compositions | | | |
|---|---|---|---|---|
| | Ingredient (wt%) | E | F | G |
| Part A: | locust bean gum | 3 | 3 | 3 |
| | sucrose stearate | 0.5 | — | 0.5 |
| | water | 74 | 75 | 74 |
| Part B: | ketoprofen | 2.5 | 2.5 | 2.5 |
| | ethanol | 15 | 15 | 15 |
| | isopropyl myristate | 5 | 5 | 5 |

EXAMPLE 8

Ketoprofen Composition H

Composition H was prepared using the ingredients listed in TABLE 3, below. The polymeric skin penetration enhancer used was the galactomannan gum, guar gum. The lipophilic solvent used was a mixture of ethanol and isopropyl myristate. Ketoprofen skin penetration was measured as described in EXAMPLE 1. The results are presented in TABLE 6, below, and in FIG. 3.

EXAMPLE 9

Ketoprofen Composition I

Figure 3:
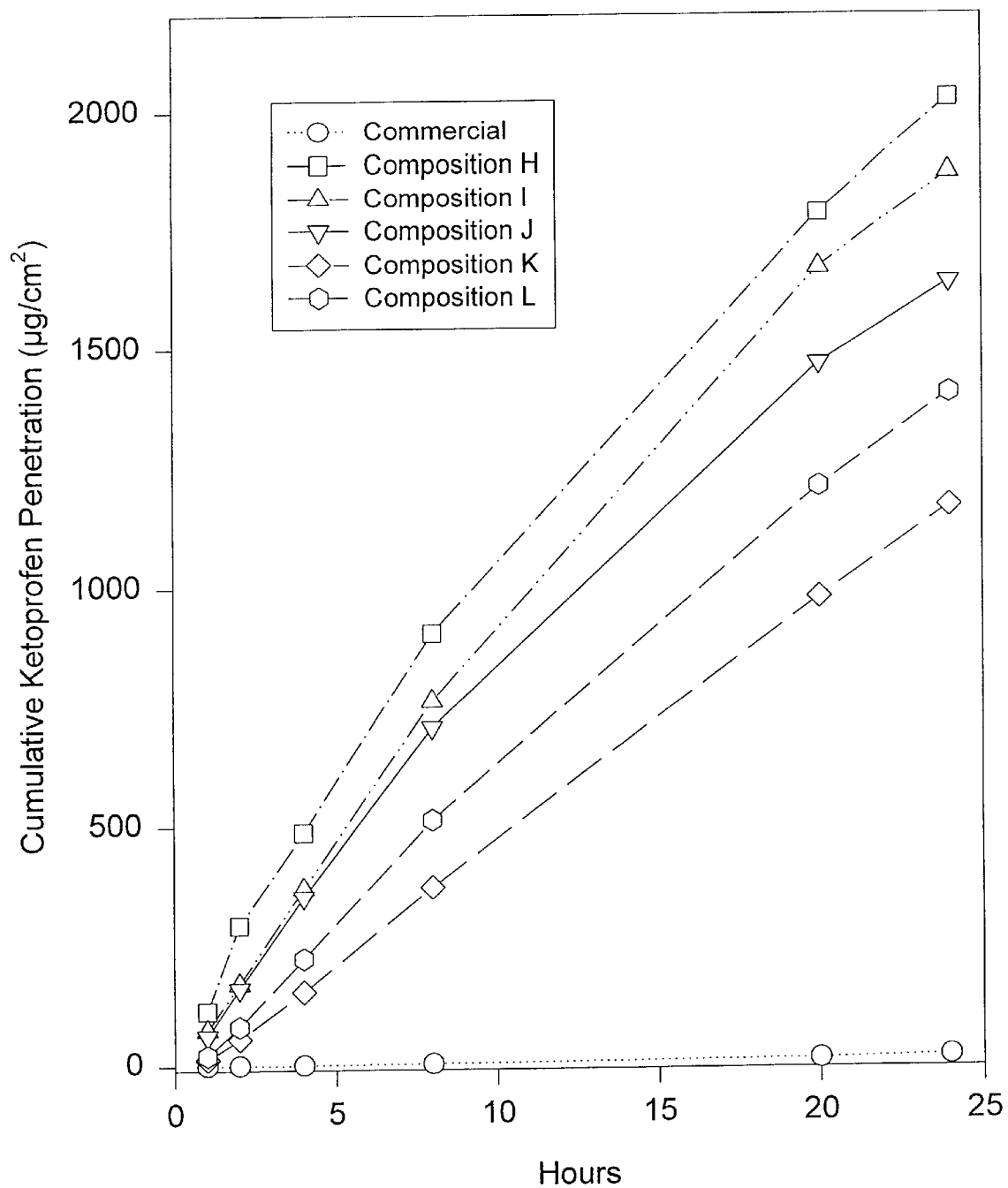
FIG. 3 is a graph of the cumulative drug penetration through shed snake skin of five additional example compositions (H through L) and the same commercial ketoprofen composition.

Composition I was prepared using the ingredients listed in TABLE 3, below. The polymeric skin penetration enhancer used was a synthetic guar gum: guar gum 2-(hydroxy-3-trimethylammonio)-propyl ether chloride aliphatic carboxylic acid. It is commercially available from Rhone-Poulenc Rorer under the designation "Jaguar C13S." The lipophilic solvent used was a mixture of ethanol and isopropyl myristate. Ketoprofen skin penetration was measured as described in EXAMPLE 1. The results are presented in TABLE 6, below, and in FIG. 3.

EXAMPLE 10

Ketoprofen Composition J

Composition J was prepared using the ingredients listed in TABLE 3, below. The skin penetration enhancer used was depolymerized cationic guar gum, which is commercially available from Rhone-Poulenc Rorer under the designation "HI CARE 1000." The lipophilic solvent used was a mixture of ethanol and isopropyl myristate. Ketoprofen skin penetration was measured as described in EXAMPLE 1. The results are presented in TABLE 6, below, and in FIG. 3.

EXAMPLE 11

Ketoprofen Composition K

Composition K was prepared using the ingredients listed in TABLE 3, below. The polymeric skin penetration enhancer used was synthetic guar gum (Jaguar C13S). The lipophilic solvent used was a mixture of ethanol and isopropyl myristate. Ketoprofen skin penetration was measured as described in EXAMPLE 1. The results are presented in TABLE 6, below, and in FIG. 3.

EXAMPLE 12

Ketoprofen Composition L

Composition L was prepared using the ingredients listed in TABLE 3, below. The polymeric skin penetration enhancer used was guar gum 2-hydroxypropyl ether. It is commercially available from Rhone-Poulenc Rorer under the designation "Jaguar HP120." The lipophilic solvent used was a mixture of ethanol and isopropyl myristate. Ketoprofen skin penetration was measured as described in EXAMPLE 1. The results are presented in TABLE 6, below, and in FIG. 3.

EXAMPLE 13

Ketoprofen Composition M

Figure 4:
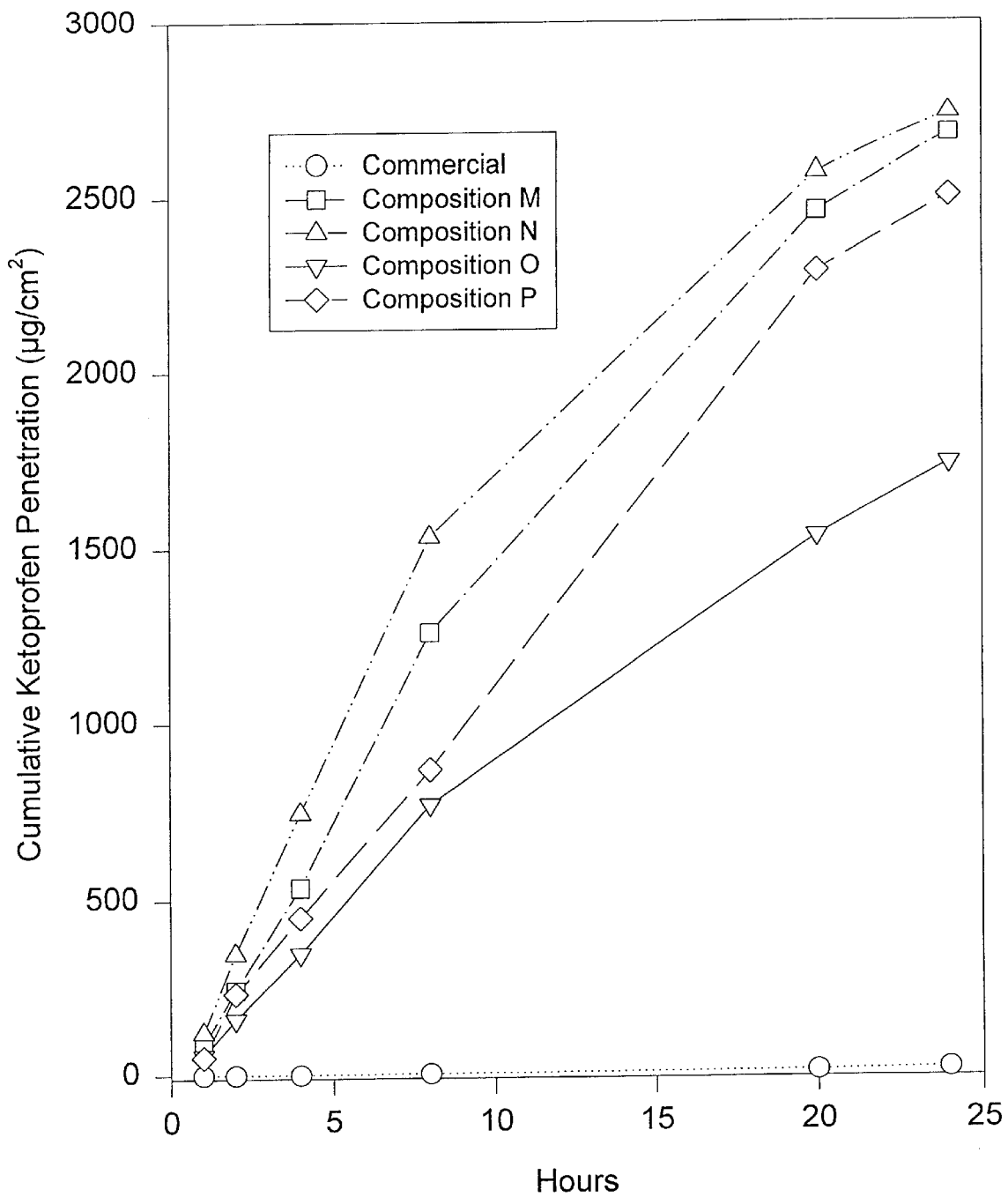
FIG. 4 is a graph of the cumulative drug penetration through shed snake skin of four more example compositions (M through P) and the same commercial ketoprofen composition.

Composition M was prepared using the ingredients listed in TABLE 3, below. The polymeric skin penetration enhancer used was synthetic guar gum (Jaguar C13S). The lipophilic solvent used was a mixture of ethanol and isopropyl myristate. Ketoprofen skin penetration was measured as described in EXAMPLE 1. The results are presented in TABLE 6, below, and in FIG. 4.

EXAMPLE 14

Ketoprofen Composition N

Composition N was prepared using the ingredients listed in TABLE 3, below. The polymeric skin penetration enhancer used was guar gum 2-hydroxy propyl ether (Jaguar HP120). The lipophilic solvent used was a mixture of ethanol and isopropyl myristate. Ketoprofen skin penetration was measured as described in EXAMPLE 1. The results are presented in TABLE 6, below, and in FIG. 3.

EXAMPLE 15

Ketoprofen Composition O

Composition O was prepared using the ingredients listed in TABLE 3, below. The polymeric skin penetration enhancer used was guar gum 2-hydroxy propyl ether (Jaguar HP120). The lipophilic solvent used was a mixture of ethanol and isopropyl myristate. Ketoprofen skin penetration was measured as described in EXAMPLE 1. The results are presented in TABLE 6, below, and in FIG. 4.

EXAMPLE 16

Ketoprofen Composition P

Composition P was prepared using the ingredients listed in TABLE 3, below. The polymeric skin penetration enhancer used was guar gum 2-hydroxy propyl ether (Jaguar HP120). The lipophilic solvent used was a mixture of ethanol and Miglyol 840. Miglyol 840 is a mixture of propylene glycol and decanoic acid, mixed diesters with octanoic acid commercially available from Huls America (Piscataway, N.J.). Ketoprofen skin penetration was measured as described in EXAMPLE 1. The results are presented in TABLE 6, below, and in FIG. 4.

TABLE 3

Ketoprofen Guar Gum Compositions

| Ingredient (wt%) | H | I | J | K | L | M | N | O | P |
|---|---|---|---|---|---|---|---|---|---|
| Part A: | | | | | | | | | |
| guar gum | 3 | — | — | — | — | — | — | 2 | 2 |
| Jaguar C13S | — | 2 | — | — | — | 2 | — | — | — |
| Jaguar HP120 | — | — | — | 2 | 2 | — | 2 | — | — |
| HI CARE 1000 | — | — | 2 | — | — | — | — | — | — |
| water | 74 | 76 | 76 | 76 | 76 | 61 | 61 | 76 | 61 |
| sucrose stearate | 0.5 | — | — | — | — | — | — | — | — |
| Part B: | | | | | | | | | |
| ketoprofen | 2.5 | 2.5 | 2.5 | 2.5 | 2.5 | 2.5 | 2.5 | 2.5 | 2.5 |
| ethanol | 15 | 15 | 15 | 15 | 15 | 30 | 30 | 15 | 30 |
| Miglyol 840 | — | — | — | — | — | — | — | — | 5 |
| isopropyl myristate | 5 | 5 | 5 | 5 | 5 | 5 | 5 | 5 | — |

EXAMPLE 17

Ketoprofen Compositions Q through U

Figure 5:
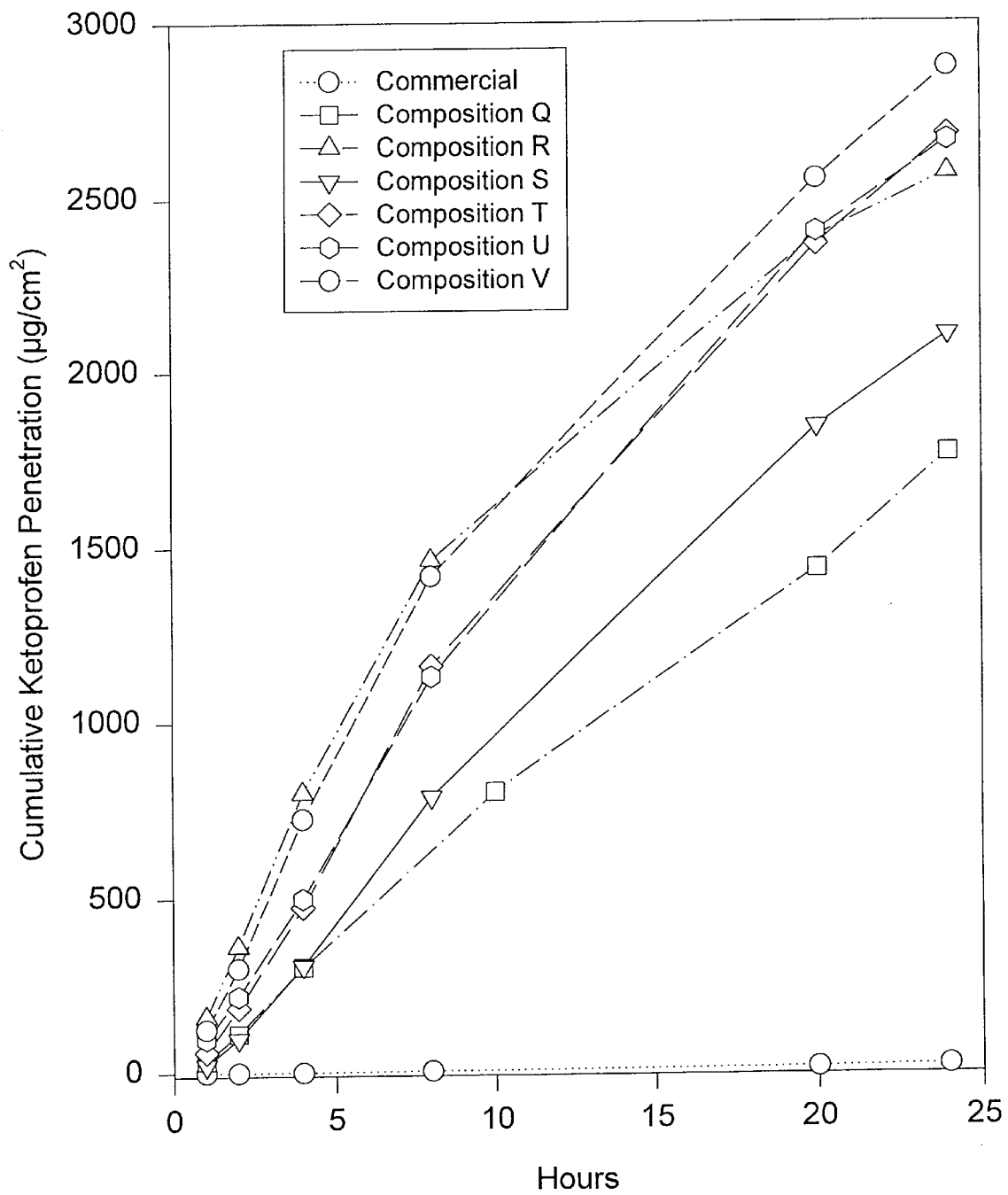
FIG. 5 is a graph of the cumulative drug penetration through shed snake skin of six additional example compositions (Q through V) and the same commercial ketoprofen composition.

Compositions Q through U were separately prepared using the ingredients listed in TABLE 4, below. The polymeric skin penetration enhancer used was xanthan gum, which is commercially available from Monsanto (San Diego, Calif.) under the designation "KELTROL T." The lipophilic solvent used was a mixture of ethanol and isopropyl myristate. Ketoprofen skin penetration was measured as described in EXAMPLE 1. The results are presented in TABLE 6, below, and in FIG. 5.

EXAMPLE 18

Ketoprofen Compositions V and W

Figure 6:
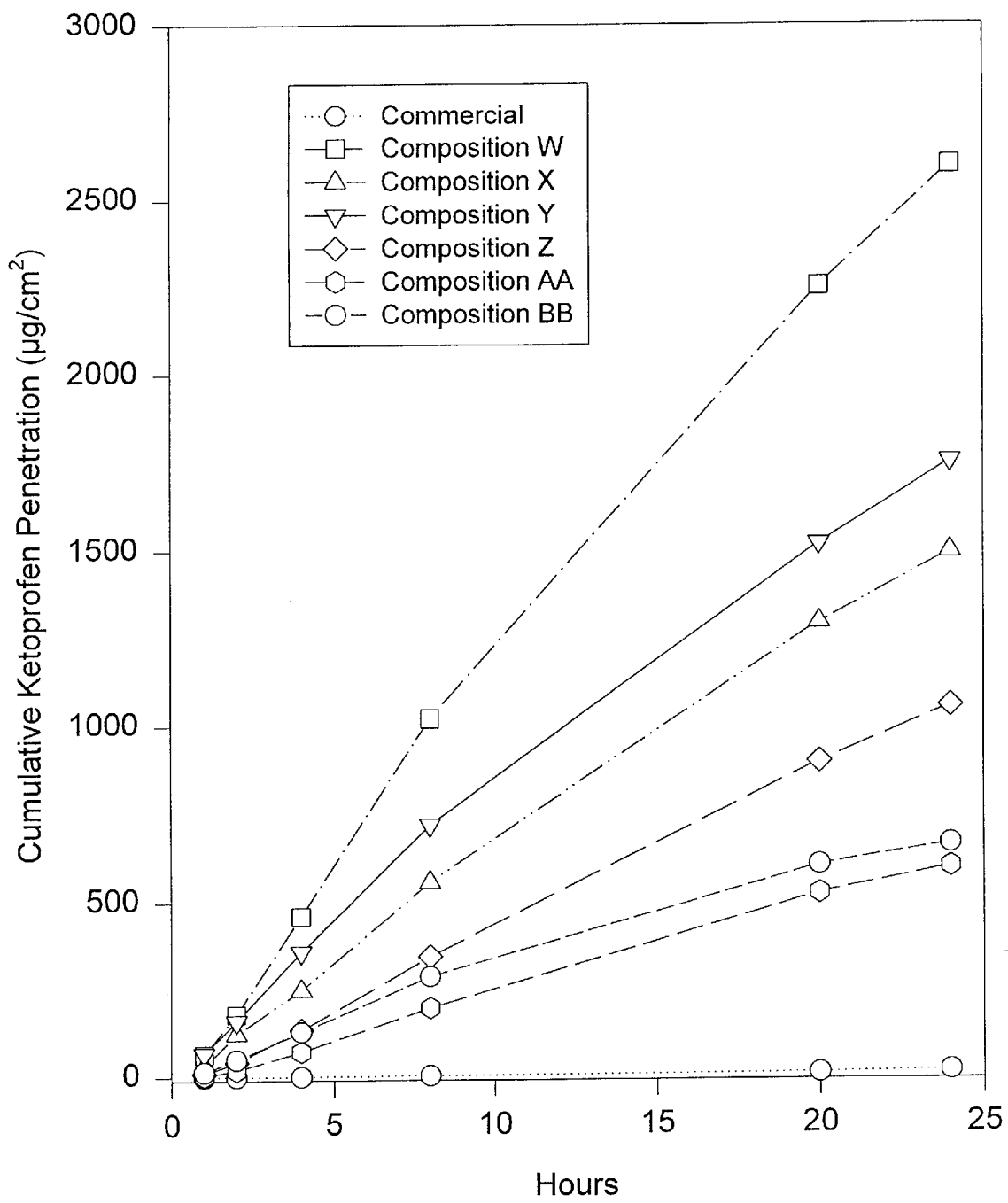
FIG. 6 is a graph of the cumulative drug penetration through shed snake skin of six more example compositions (W through BB) and the same commercial ketoprofen composition.

Compositions V and W were separately prepared using the ingredients listed in TABLE 4, below. The polymeric skin penetration enhancer used was xanthan gum (KELTROL T). The lipophilic solvent used was a mixture of ethanol, propylene glycol and isopropyl myristate. Ketoprofen skin penetration was measured as described in EXAMPLE 1. The results are presented in TABLE 6, below, and in FIGS. 5 and 6.

EXAMPLE 19

Ketoprofen Compositions X through Z

Compositions X through Z were separately prepared using the ingredients listed in TABLE 4, below. The polymeric skin penetration enhancer used was xanthan gum (KELTROL T). The lipophilic solvent used was a mixture of ethanol and isopropyl myristate. Ketoprofen skin penetration was measured as described in EXAMPLE 1. The results are presented in TABLE 6, below, and in FIG. 6.

EXAMPLE 20

Ketoprofen Composition AA

Composition AA was prepared using the ingredients listed in TABLE 4, below. The polymeric skin penetration enhancer used was xanthan gum (KELTROL T). The lipophilic solvent used was a mixture of propylene glycol and Miglyol 810, a capric/caprylic triglyceride solution commercially available from Huls America (Piscataway, N.J.). Ketoprofen skin penetration was measured as described in EXAMPLE 1. The results are presented in TABLE 6, below, and in FIG. 6.

EXAMPLE 21

Ketoprofen Composition BB

Composition BB was prepared using the ingredients listed in TABLE 4, below. The polymeric skin penetration enhancer used was xanthan gum (KELTROL T). The lipophilic solvent used was a mixture of ethanol and mixed diesters with octanoic acid and decanoic acid (Miglyol 840). Ketoprofen skin penetration was measured as described in EXAMPLE 1. The results are presented in TABLE 6, below, and in FIG. 6.

TABLE 4

Ketoprofen Xanthan Gum Compositions

| | Ingredient (wt%) | Q | R | S | T | U | V |
|---|---|---|---|---|---|---|---|
| Part A: | xanthan gum | 2 | 2 | 2 | 2 | 2 | 2 |
| | water | 61 | 61 | 61 | 61 | 61 | 61 |
| Part B: | ketoprofen | 2.5 | 2.5 | 2.5 | 2.5 | 2.5 | 2.5 |
| | ethanol | 30 | 30 | 30 | 30 | 30 | 10 |
| | isopropanol | — | — | — | — | — | 10 |

TABLE 4-continued

| | propylene glycol | — | — | — | — | — | 10 |
|---|---|---|---|---|---|---|---|
| | isopropyl myristate | 5 | 5 | 5 | 5 | 5 | 5 |

| | Ingredient (wt%) | W | X | Y | Z | AA | BB |
|---|---|---|---|---|---|---|---|
| Part A: | xanthan gum | 2 | 2 | 2 | 2 | 2 | 2 |
| | water | 61 | 76 | 76 | 76 | 61 | 61 |
| Part B: | ketoprofen | 2.5 | 2.5 | 2.5 | 2.5 | 2.5 | 2.5 |
| | ethanol | 10 | 15 | 15 | 15 | 30 | 30 |
| | isopropanol | 10 | — | — | — | — | — |
| | propylene glycol | 10 | — | — | — | — | — |
| | Miglyol 810 | — | — | — | — | 5 | — |
| | Miglyol 840 | — | — | — | — | — | 5 |
| | isopropyl myristate | 5 | 5 | 5 | 5 | — | — |

EXAMPLE 22

Ketoprofen Composition CC

Figure 7:
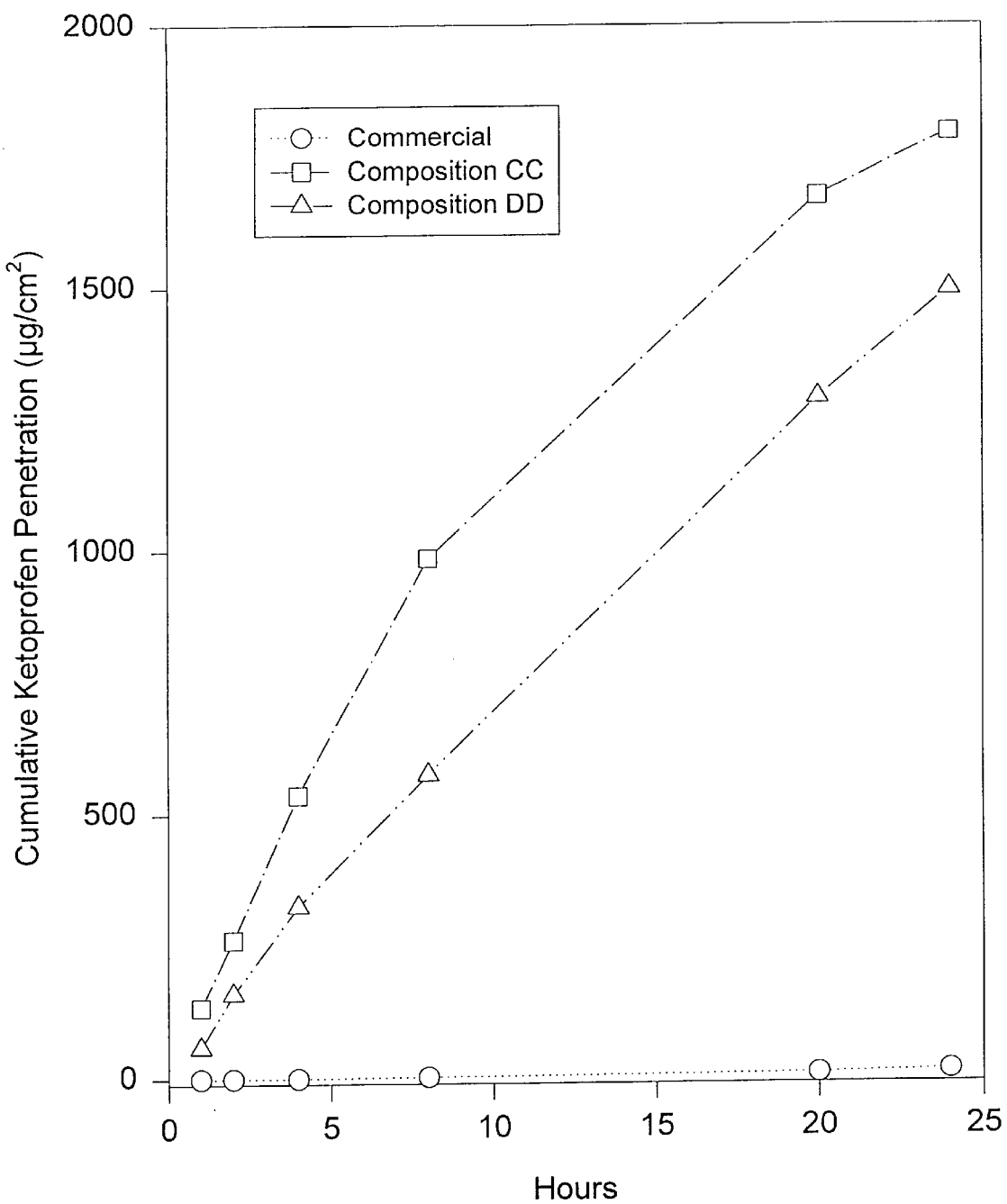
FIG. 7 is a graph of the cumulative drug penetration through shed snake skin of two additional example compositions (CC through DD) and the same commercial ketoprofen composition.

Composition CC was prepared using the ingredients listed in TABLE 5, below. The polymeric skin penetration enhancer used was hydroxypropyl methylcellulose, which is commercially available from Dow Chemical Company (Midland, Mich.) under the designation "Methocel E4M Premium, NF". The lipophilic solvent used was a mixture of ethanol and isopropyl myristate. Ketoprofen skin penetration was measured as described in EXAMPLE 1. The results are presented in TABLE 6, below, and in FIG. 7.

EXAMPLE 23

Ketoprofen Composition DD

Composition CC was prepared using the ingredients listed in TABLE 5, below. The polymeric skin penetration enhancer used was propylene glycol alginate. The lipophilic solvent used was a mixture of ethanol and isopropyl myristate. Ketoprofen skin penetration was measured as described in EXAMPLE 1. The results are presented in TABLE 6, below, and in FIG. 7.

TABLE 5

Ketoprofen Compositions

| | Ingredient (wt%) | CC | DD |
|---|---|---|---|
| Part A: | methylcellulose | 3 | — |
| | PG alginate | — | 3 |
| | water | 60 | 76 |
| Part B: | ketoprofen | 2.5 | 2.5 |
| | ethanol | 30 | 15 |
| | isopropyl myristate | 5 | 5 |

EXAMPLE 24

Comparison of Penetration Profiles

The cumulative amount of ketoprofen penetration were determined as described in Example 1. The results are presented in TABLE 6, below, and in FIGS. 1 through 7.

TABLE 6 shows the cumulative amount of ketoprofen penetrating after 1, 2, 4, 8, 20 and 24 hours for each example composition according to the present invention as well as for the commercially available sample (Profenid). These data demonstrate the superior ability of the present invention to delivery NSAI drugs transdermally when compared to heretofore available compositions. FIGS. 1 through 7 are graphs generated from the data presented in TABLE 6. Significantly, and well represented in graphical form, compositions according to the present invention deliver effective skin penetration by ketoprofen relatively faster than the commercial composition.

| -continued | |
|---|---|
| hydroxypropylcellulose | 2 wt % |
| water | 20 wt % |

The ketoprofen skin penetration of these comparative examples was measured as described in EXAMPLE 1. The results are presented in TABLE 7, below.

TABLE 6

Cumulative Ketoprofen Penetration ($\mu g/cm^2$)

| Hour | Commercial | A | B | C | D | E | F | G | H | I | J | K | L | M | N |
|---|---|---|---|---|---|---|---|---|---|---|---|---|---|---|---|
| 1 | 0 | 145 | 80 | 59 | 81 | 113 | 85 | 48 | 115 | 74 | 63 | 14 | 21 | 87 | 121 |
| 2 | 0 | 392 | 207 | 142 | 200 | 334 | 246 | 141 | 293 | 171 | 161 | 55 | 81 | 245 | 347 |
| 4 | 0 | 650 | 417 | 312 | 487 | 520 | 402 | 351 | 487 | 370 | 352 | 153 | 223 | 535 | 745 |
| 8 | 2.1 | 1432 | 698 | 631 | 1021 | 976 | 802 | 696 | 903 | 761 | 705 | 372 | 511 | 1257 | 1532 |
| 18 | — | 2222 | 1735 | 1163 | 1785 | — | — | — | | | | | | | |
| 20 | 7.8 | — | — | — | — | 1947 | 1755 | 1321 | 1781 | 1666 | 1465 | 976 | 1208 | 2458 | 2568 |
| 24 | 13.1 | 2410 | 2019 | 1405 | 1979 | 2229 | 2048 | 1515 | 2024 | 1865 | 1635 | 1167 | 1403 | 2677 | 2738 |

| Hour | O | P | Q | R | S | T | U | V | W | X | Y | Z | AA | BB | CC | DD |
|---|---|---|---|---|---|---|---|---|---|---|---|---|---|---|---|---|
| 1 | 57 | 51 | 34 | 160 | 23 | 59 | 96 | 125 | 64 | 31 | 66 | 9 | 3 | 14 | 136 | 60 |
| 2 | 160 | 233 | 112 | 362 | 97 | 186 | 220 | 299 | 178 | 122 | 160 | 41 | 19 | 49 | 263 | 161 |
| 4 | 347 | 450 | 302 | 798 | 306 | 473 | 498 | 725 | 460 | 248 | 358 | 134 | 71 | 128 | 536 | 327 |
| 8 | 768 | 867 | 800* | 1463 | 785 | 1159 | 1130 | 1417 | 1020 | 556 | 718 | 343 | 197 | 287 | 986 | 575 |
| 20 | 1531 | 2287 | 1434 | 2386 | 1840 | 2362 | 2400 | 2552 | 2250 | 1290 | 1516 | 896 | 522 | 602 | 1674 | 1290 |
| 24 | 1738 | 2501 | 1764 | 2569 | 2103 | 2677 | 2660 | 2872 | 2595 | 1491 | 1749 | 1052 | 596 | 663 | 1793 | 1495 |

*Measured at 10 Hours for Composition Q.

To further assess the effectiveness of compositions according the present invention, comparative example compositions were prepared according to the disclosure in U.S. Pat. No. 5,093,133 to Wisniewski et al. (Comparative Composition 1) and U.S. Pat. No. 4,393,076 to Noda et al (Comparative Composition 2). Specifically, the following ingredients were used.

| Comparative Composition 1: | |
|---|---|
| ketoprofen | 2.5 wt % |
| ethanol | 44.2 wt % |
| water | 37.5 wt % |
| methyl paraben | 0.1 wt % |
| methyl paraben | 0.1 wt % |
| hydroxypropylcellulose | 2.5 wt % |
| triethanolamine | 0.25 wt % |
| Comparative Composition 2: | |
| CARBOPOL 940 ® | |
| ketoprofen | 2.5 wt % |
| ethanol | 30 wt % |
| propylene glycol | 30 wt % |
| propylene carbonate | 15 wt % |

TABLE 7

Comparative Examples
Cumulative Ketoprofen Penetration ($\mu g/cm^2$)

| Hour | Comparative Composition 1 | Comparative Composition 2 |
|---|---|---|
| 1 | 0 | 0 |
| 2 | 0 | 0 |
| 4 | 4 | 0.4 |
| 8 | 15 | 5.5 |
| 20 | 73 | 36 |
| 24 | 103 | 64 |

Figure 8:
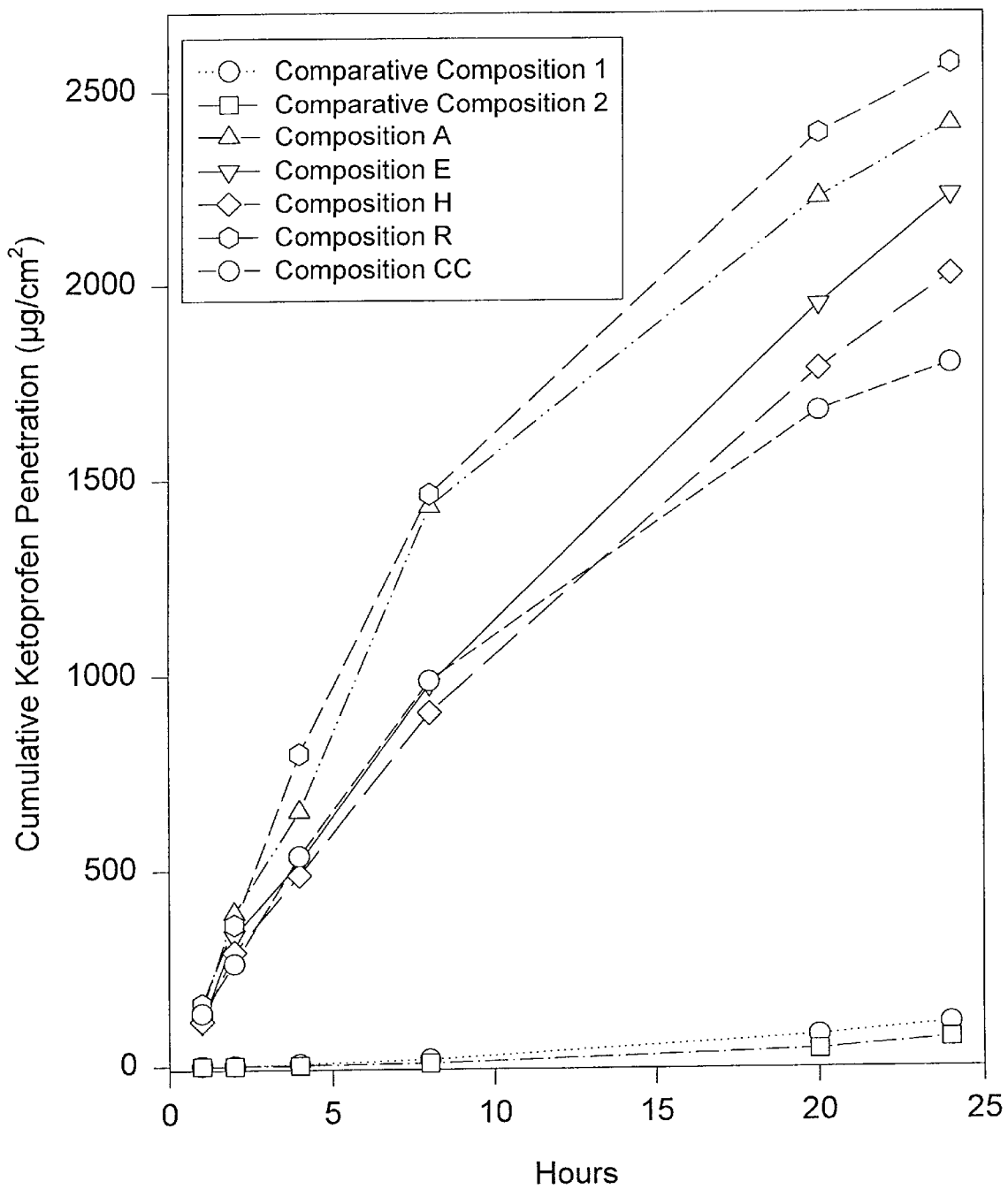
FIG. 8 is a graph of cumulative drug penetration through shed snake skin of selected ketoprofen compositions prepared according to the present invention and two known ketoprofen compositions.

The data of TABLE 7 are compared graphically to selected compositions in FIG. 8. The penetration data demonstrate that compositions according to the present invention deliver relatively more NSAI drug, relatively faster than the comparative prior art compositions.

EXAMPLE 25

Ibuprofen Composition EE

Composition EE was prepared using the ingredients listed in TABLE 8, below. The polymeric skin penetration enhancer used was polyacrylic acid polymer (CARBOPOL® 940). The lipophilic solvent used was a mixture of ethanol and isopropyl myristate. Ibuprofen skin penetration was measured as described in EXAMPLE 1 using the same techniques applied for ketoprofen.

Figure 9:
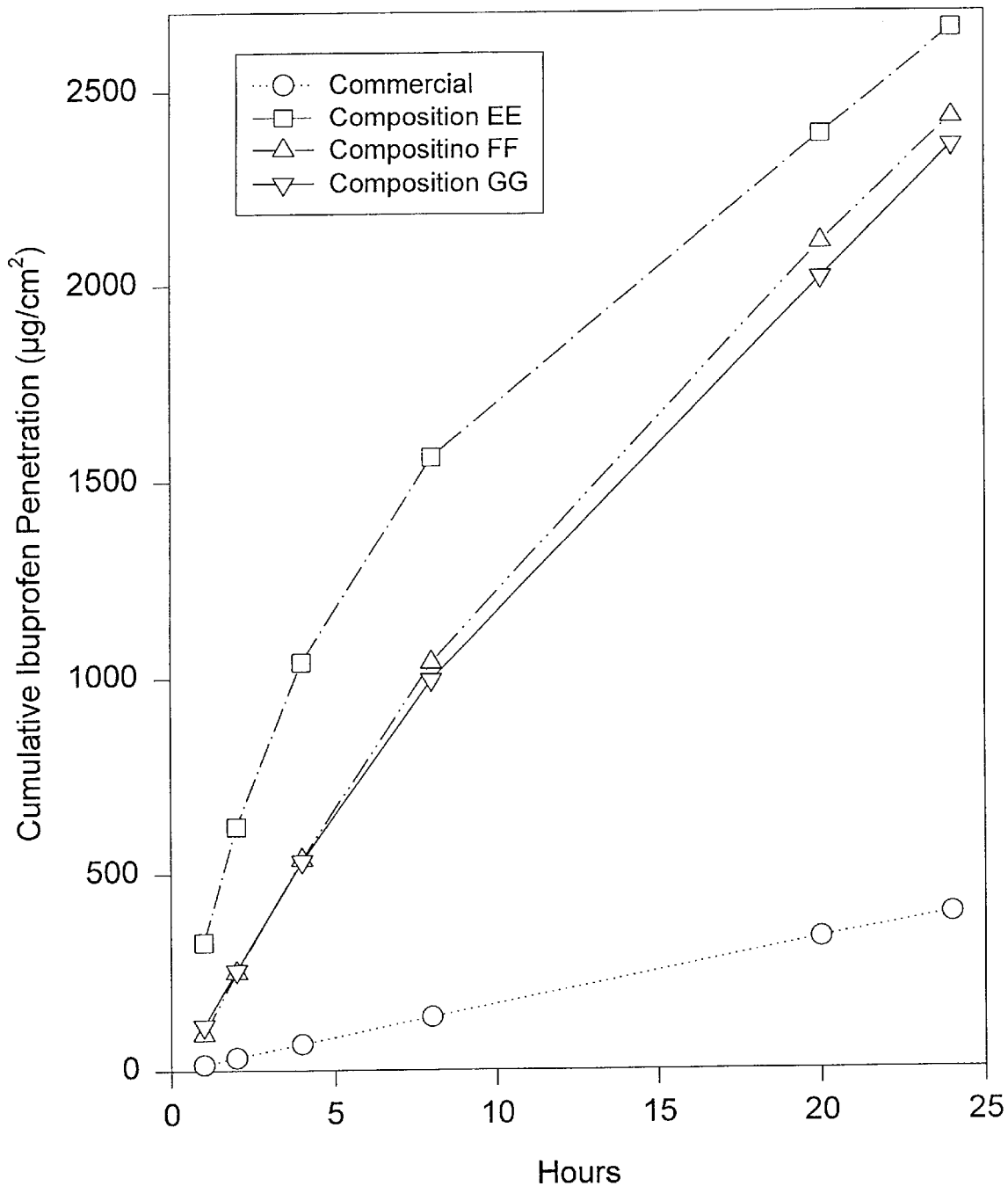
FIG. 9 is a graph of cumulative drug penetration through shed snake skin of three topical ibuprofen compositions prepared according to the present invention and a commercial ibuprofen composition.

The penetration of ibuprofen from Composition EE was compared to a commercial topical Ibuleve preparation (Diomed Development Ltd. (Hitchin, United Kingdon). The ibuprofen from Composition EE penetrated relatively faster compared to the commercial composition. The results of the penetration study are presented in TABLE 9, below, and in FIG. 9.

EXAMPLE 26

Ibuprofen Composition FF

Composition FF was prepared using the ingredients listed in TABLE 8, below. The polymeric skin penetration enhancer used was xanthan gum (KELTROL T). The lipophilic solvent used was a mixture of ethanol and isopropyl myristate. Ibuprofen skin penetration was measured as described in EXAMPLE 1. The results are presented in TABLE 9, below, and in FIG. 9.

The ibuprofen from Composition FF penetrated relatively faster compared to the commercial composition.

EXAMPLE 27

Ibuprofen Composition GG

Composition GG was prepared using the ingredients listed in TABLE 8, below. The polymeric skin penetration enhancer used was xanthan gum (KELTROL T). The lipophilic solvent used was a mixture of ethanol, isopropanol and isopropyl myristate. The results are presented in TABLE 9, below, and in FIG. 9.

The ibuprofen from Composition GG penetrated relatively faster compared to the commercial composition.

TABLE 8

Ibuprofen Compositions

| | Ingredient (wt%) | EE | FF | GG |
|---|---|---|---|---|
| Part A: | CARBOPOL 940 ® | 2 | — | — |
| | xanthan gum | — | 2 | 2 |
| | water | 63 | 63 | 63 |
| Part B: | ibuprofen | 5 | 5 | 5 |
| | ethanol | 30 | 30 | 15 |
| | isopropanol | — | — | 15 |
| | isopropyl myristate | 5 | 5 | 5 |

TABLE 9

Cumulative Ibuprofen Penetration ($\mu g/cm^2$)

| Hour | Commercial | EE | FF | GG |
|---|---|---|---|---|
| 1 | 14 | 327 | 92 | 114 |
| 2 | 32 | 620 | 250 | 255 |
| 4 | 66 | 1039 | 536 | 532 |
| 8 | 135 | 1561 | 1039 | 994 |
| 20 | 334 | 2383 | 2105 | 2015 |
| 24 | 397 | 2657 | 2426 | 2352 |

EXAMPLE 28

Comparison Using Human Skin

To further asses the effectiveness of compositions according the present invention the commercial ketoprofen topical composition (Profenid) and Composition Q were tested for ketoprofen penetration using human skin.

Figure 10:
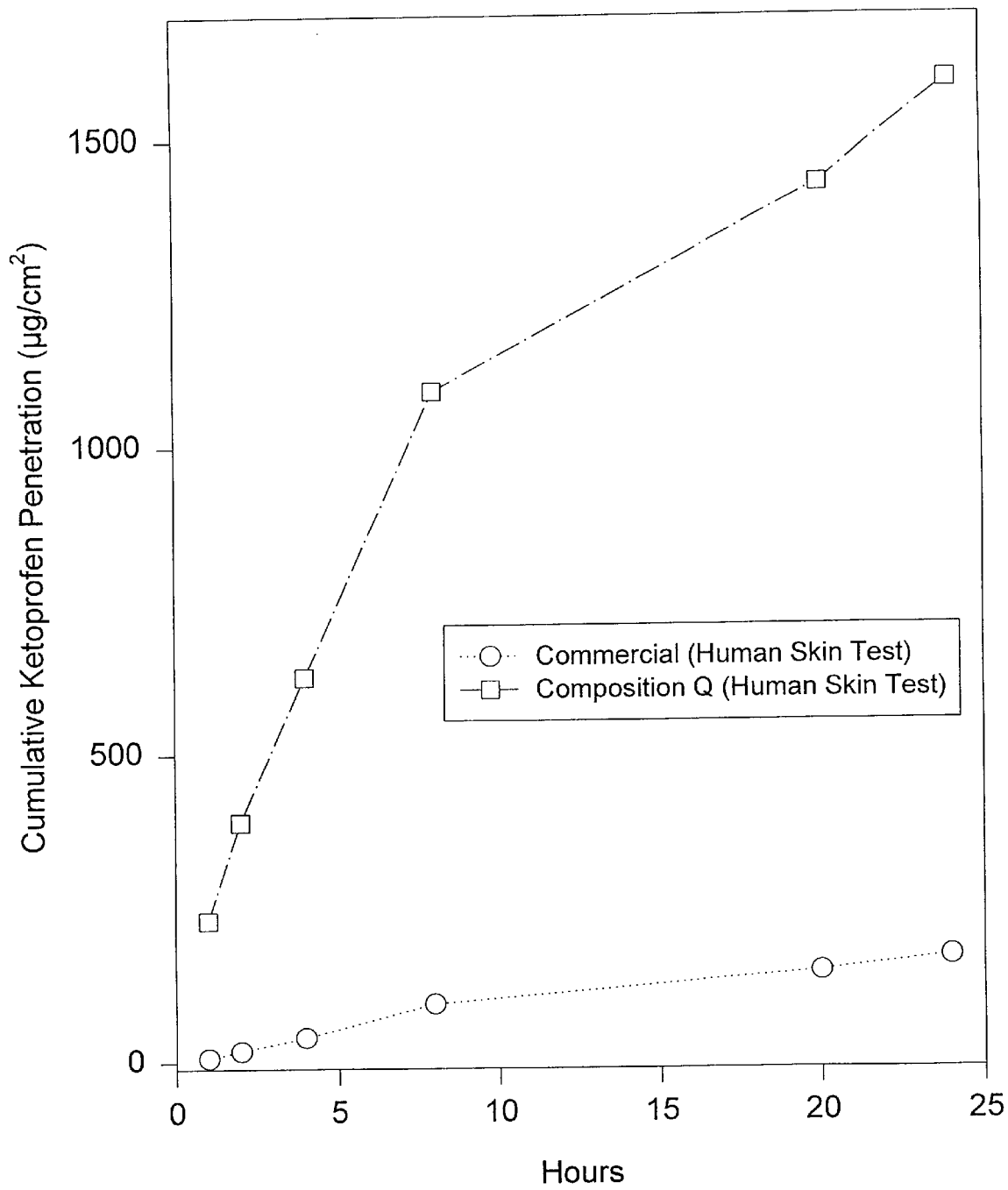
FIG. 10 is a graph of cumulative drug penetration through human skin of a commercial ketoprofen composition and a ketoprofen composition prepared according to the present invention.

Specifically, human breast skin samples were prepared using the heat separation technique. Skin samples were immersed in water at 60° C. for 60 seconds. The epidermal membranes were carefully teased off the underlying dermis and washed with water. After air drying, the samples were placed in a desiccator for 24 hours and then stored in a freezer. Before testing, skin pieces were removed from the freezer, held at room temperature for 4 hours, and hydrated for 30 minutes in a buffer solution. The pieces were next mounted into Franz-type Diffusion cells (surface area 1.8 $cm^2$) and evaluated as described in EXAMPLE 1. The results are tabulated below (TABLE 10) and given graphically in FIG. 10.

TABLE 10

Human Skin Testing
Cumulative Ketoprofen Penetration ($\mu g/cm^2$)

| Hour | Composition Q | Commercial |
|---|---|---|
| 1 | 34 | 0 |
| 2 | 112 | 0 |
| 4 | 302 | 0 |
| 8 | 800 | 2 |
| 20 | 1434 | 8 |
| 24 | 1764 | 13 |

Confirming the results of the snake skin tests, Composition Q delivers ketoprofen relatively faster and to a greater extent than the commercially available composition.

The foregoing is intended to be illustrative of the present invention, but not limiting. Numerous variations and modifications may be effected without departing from the true spirit and scope of the invention.

We claim:

1. An aqueous pharmaceutical composition having an improved skin penetration effect, suitable for topical application, having a semi-solid consistency, and comprising:

a non-steroidal anti-inflammatory drug present in the amount of about 0.1 to about 10 percent based on the weight of the composition;

a non-basic polymeric skin penetration enhancer present in an amount sufficient to enhance skin penetration of said anti-inflammatory drug, said polymeric skin penetration enhancer being a member of the group consisting of a water-dispersible acid polymer, a polysaccharide gum, and a mixture thereof; and a carrier consisting essentially of water and a lipophilic solvent which is a mixture of an aliphatic $C_2$ to $C_8$ alcohol and an aliphatic $C_8$ to $C_{30}$ ester, said lipophilic solvent being present in an amount of about 10 percent to about 40 percent;

the composition having the ratio of the amount by weight of said aliphatic $C_2$ to $C_8$ alcohol to the amount by weight of said $C_2$ to $C_8$ ester in the range of about 1 to about 7.

2. The composition in accordance with claim 1 wherein said anti-inflammatory drug is an ibufenac group drug.

3. The composition in accordance with claim 1 wherein said anti-inflammatory drug is an arylpropionic acid derivative.

4. The composition in accordance with claim 1 wherein said non-steroidal anti-inflammatory drug is a member of the grouping consisting of cliprofen, fenoprofen, fluprofen, ibuprofen, ketoprofen, fenbufen, alcofenac, amfenac sodium, fenclofenac, ibufenac, naproxen, naproxol, and diflunisal.

5. The composition in accordance with claim 1 wherein said anti-inflammatory drug is ketoprofen.

6. The composition in accordance with claim 1 wherein said anti-inflammatory drug is ibuprofen.

7. The composition in accordance with claim 1 wherein said anti-inflammatory drug is piroxicam.

8. The composition in accordance with claim 1 wherein said polymeric skin penetration enhancer is polyacrylic acid.

9. The composition in accordance with claim 1 wherein said polymeric skin penetration enhancer is a carbomer.

10. The composition in accordance with claim 1 wherein said polymeric skin penetration enhancer is a galactomannan gum.

11. The composition in accordance with claim 10 wherein said galactomannan gum is guar gum.

12. The composition in accordance with claim 10 wherein said galactomannan gum is locust bean gum.

13. The composition in accordance with claim 1 wherein said polymeric skin penetration enhancer is a polysaccharide gum selected from the group consisting of agar gum, alginate, carob gum, carrageen gum, ghatti gum, guar gum, karaya gum, kadaya gum, locust bean gum, rhamsan gum, xanthan gum, and a mixture thereof.

14. The composition in accordance with claim 1 wherein said polymeric skin penetration enhancer is a cellulose derivative.

15. The composition in accordance with claim 14 wherein said cellulose derivative is selected from the group consisting of ethyl cellulose, methyl cellulose, hyrdoxypropyl cellulose, and mixtures thereof.

16. The composition in accordance with claim 1 wherein said aliphatic $C_2$ to $C_8$ alcohol is selected from the group consisting of ethanol, n-propanol, isopropanol, propylene glycol, glycerol, and a mixture thereof.

17. The composition in accordance with claim 1 wherein said aliphatic $C_2$ to $C_{30}$ ester is selected from the group consisting of ethyl acetate, butyl acetate, ethyl laurate, methyl propionate, ethyl propionate, isopropyl myristate, isopropyl palmitate, and a mixture thereof.

18. The composition in accordance with claim 1 further including a buffer system capable of providing a buffered pH value for said composition in the range of about 3 to about 7.4.

* * * * *

UNITED STATES PATENT AND TRADEMARK OFFICE
CERTIFICATE OF CORRECTION

PATENT NO.    : 6,083,996
DATED         : July 4, 2000
INVENTOR(S)   : Servet Büyüktimkin et al.

It is certified that error appears in the above-identified patent and that said Letters Patent is hereby corrected as shown below:

Claim 1,
Line 21, "$C_2$ to $C_8$ ester" should be -- $C_8$ to $C_{30}$ ester --.

Signed and Sealed this

Fifteenth Day of January, 2002

Attest:

JAMES E. ROGAN
Attesting Officer
Director of the United States Patent and Trademark Office